United States Patent [19]

Akhavi

[11] 4,237,883
[45] Dec. 9, 1980

[54] NEEDLE PACKAGE AND METHOD OF TREATING SYRINGE

[75] Inventor: David S. Akhavi, Los Angeles, Calif.

[73] Assignee: American Hospital Supply Corporation, Evanston, Ill.

[21] Appl. No.: 26,118

[22] Filed: Apr. 2, 1979

[51] Int. Cl.³ ............................................. A61M 5/00
[52] U.S. Cl. .............................. 128/218 N; 128/221; 206/365
[58] Field of Search ............... 128/763, 218 R, 218 N, 128/215, 216, 221; 206/365

[56] References Cited

U.S. PATENT DOCUMENTS

| 1,007,804 | 11/1911 | Schimmel | 206/365 X |
| 2,400,722 | 5/1946 | Swan | 128/215 X |
| 3,333,682 | 8/1967 | Burke | 206/365 |
| 3,934,722 | 1/1976 | Goldberg | 206/365 |
| 4,124,025 | 11/1978 | Alrazi | 128/218 R |

Primary Examiner—John D. Yasko
Attorney, Agent, or Firm—Larry N. Barger

[57] ABSTRACT

A needle package which can contain any one of various sizes of needles and can be sold independently of a hypodermic syringe. The needle package includes a conventional needle protector fitted with a hypodermic needle and a closure. Within the protector is a syringe treating liquid, such as an anticoagulant (heparin), for treating a syringe immediately prior to collecting a blood sample. The same needle used for treating the syringe is also used for collecting a blood sample after removal of the protector.

14 Claims, 4 Drawing Figures

FIG. 1 (PRIOR ART)
FIG. 2
FIG. 3
FIG. 4
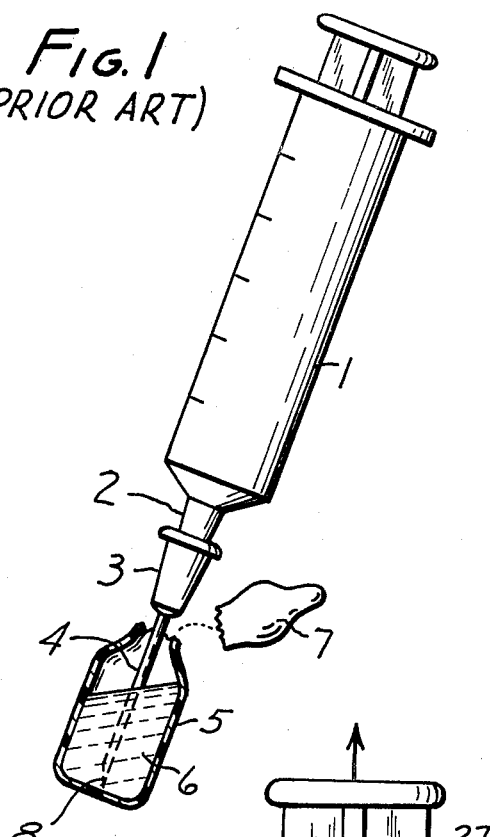
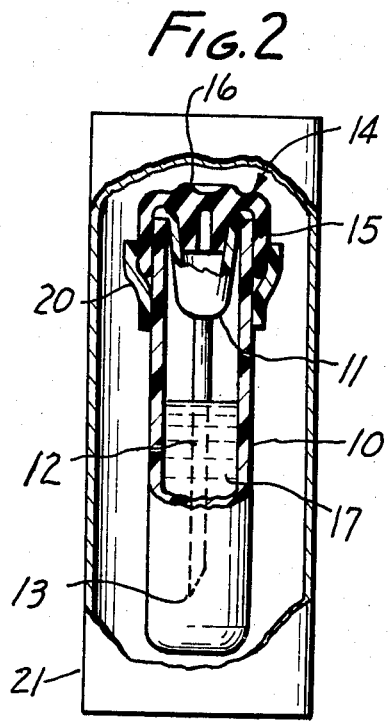
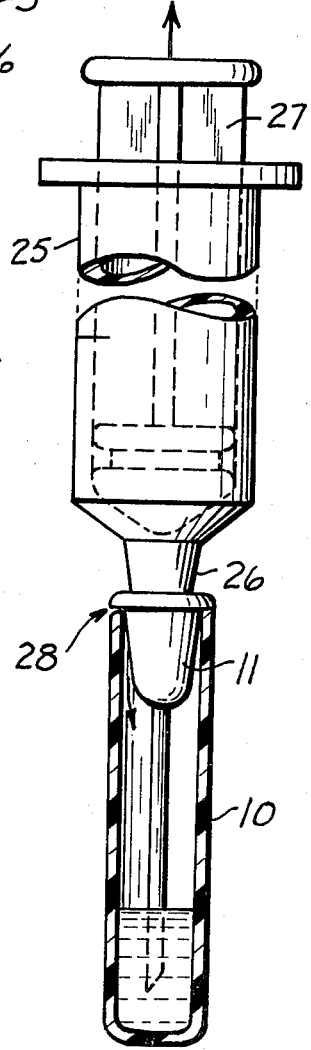
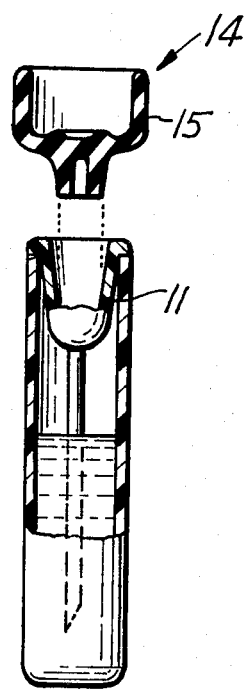

NEEDLE PACKAGE AND METHOD OF TREATING SYRINGE

BACKGROUND

In collecting a blood sample from an artery or vein of a patient, it is necessary to treat the hypodermic syringe with an anticoagulant, such as in U.S. Pat. No. 4,057,052. The conventional way of treating such a syringe is shown in FIG. 1 where the neck of a glass vial containing an anticoagulant is broken off and an interior of the syringe treated with anticoagulant. Such glass vials have the disadvantage of dulling the puncturing tip of the needle when it touches the bottom of the vial and exhibiting sharp edges of the vial neck which can cut an operator.

In the past, it has been proposed to package a particular injectable medicine and syringe together as a unit. This was often used in "wet-dry" mixtures in which a liquid component and powder component were separated until immediately prior to use when they were mixed. Because such combined syringe and injectable medicine container were coupled as a unit, there was no possibility of interchanging needle sizes, etc. with a particular coupled unit. Such needles were formed as an integral part of the syringe itself, as shown in U.S. Pat. Nos. 2,666,434; 2,772,677; 3,397,694; and 3,630,199.

It has also been proposed to package a needle with a dry powder in its hub for mixing with liquid in a hypodermic syringe for reconstituting a freeze dried drug, as in U.S. Pat. No. 3,696,579. However, since the needle hub was of very limited capacity, it could not be conveniently used to contain sufficient liquid anticoagulant for treating an inner surface of a syringe prior to collecting a blood sample. Instead, the purpose of this patent was to inject a reconstituted drug, and not to collect and store a blood sample.

Along this same line of preparing for injecting a patient, U.S. Pat. No. 3,563,240 describes a needle adapter of a syringe used to puncture the membrane of an elongated vial like device containing penicillin, which is then injected through a nozzle of the elongated vial along with the given dose of a supplemental medication from the syringe. There is no mention in the patent of a device to treat the syringe barrel with a liquid, such as an anticoagulant, immediately prior to collecting a blood sample.

U.S. Pat. No. 3,876,771 describes a flexible syringe with a needle protector containing a liquid which is poured over a patient's skin to disinfect it prior to injection. There is no indication that the needle is or can be sold separately from the collapsible syringe.

One other U.S. Pat. No. 3,905,366, has a double ended needle with a protector having what appears to be certain internal hash marks, but there is no indication as to what these are or whether the protector contains a liquid and if so, what the liquid is for. These hash marks could well be shading for the internal surface of an empty protector. In any event, they fail to teach a device which can be sold separately from a hypodermic syringe and be used to internally treat such syringe with a liquid, such as an anticoagulant, immediately prior to collecting a blood sample.

SUMMARY OF THE INVENTION

The present invention overcomes the problem of conveniently providing a treatment, such as with liquid anticoagulant, to a hypodermic syringe immediately prior to collecting a blood sample. The anticoagulant is stored within a conventional protector that contains a hypodermic needle and a sealing closure for the protector and needle. Prior to collecting a blood sample, the closure is open and the cannula attached to the hypodermic syringe. Retracting a plunger of the syringe causes air to enter at a vent between the protector and needle hub as anticoagulant is sucked into the syringe barrel where it treats the barrel's interior for receiving a blood sample. Removal of the protector provides a treated syringe with attached needle ready for puncture of a vein or artery.

THE DRAWINGS

FIG. 1 is a front elevational view of a conventional hypodermic syringe being filled with an anticoagulant from a glass vial according to present procedure;

FIG. 2 is a partially sectioned front view of the needle package of the present invention showing it encased in an outer hermetic enclosure;

FIG. 3 is a front elevational view partially in section showing the closure being removed; and FIG. 4 is a front elevational view partially in section showing the syringe in the process of being treated with an anticoagulant.

DETAILED DESCRIPTION

In FIG. 1, a conventional syringe 1 has an adapter 2 connected to a needle hub 3 that is joined in turn to a sharpened cannula 4. This cannula 4 is inserted into a glass vial 5 containing an anticoagulant, such as heparin 6. As shown, the glass vial 5 has previously been broken apart at its neck to remove a head section 7. In addition to leaving a jagged glass edge at the neck which could cut an operator, the glass vial can also dull the sharpened end 8 of cannula 4 when jammed against the bottom of the glass vial 5.

The problems described above are avoided by the needle package of the present invention shown in FIG. 2. Here a conventional needle protector 10 encases a conventional hypodermic needle which includes a hub 11 and a cannula 12. Because of the physical relationship of the cannula 12 and bottom end of protector 10, the cannula's sharpened tip 13 is not damaged. Also, during insertion of the needle into protector 10, there is little likelihood of damaging the needle, because the protector 10 is preferably of a thermoplastic material substantially softer than glass. Sealing off the needle hub 11 and protector 10 is a closure 14 that can include an upper wall and a depending skirt 15 that seals off the juncture between hub 11 with an upper end of protector 10. This closure can be of a rubber material, and if desired, includes an upstanding target ring if for some reason the closure needed to be punctured to extract a small amount of a syringe treating liquid, such as the anticoagulant heparin 17, from protector 10. Also, this closure could be used to inject a small amount of additional medication into the anticoagulant 17.

To insure a complete seal at the closure and to indicate if any tampering has been done with this seal, a tear-off shrink band 20 could be employed. Also, to prevent any vapor transmission across the plastic protector 10 which could alter the strength of the anticoagulant, the entire needle package is preferably encased in a vapor barrier pouch 21 until immediately ready for use. Vapor barrier pouch 21 could be of an aluminum foil material.

When ready to treat the hypodermic syringe, the needle package is removed from protective pouch 21 and the skirt 15 inverted to the position shown in FIG. 3 and the closure 14 removed from needle hub 11. The syringe, such as 25, is connected at a needle adapter 26 to hub 11. Upon retraction of plunger 27, air is drawn into protector 10 through conventional gas sterilizing vent structure as shown at 28. A gas sterilizing vent structure utilizing ribs is shown in U.S. Pat. No. 3,112,747.

When sufficient anticoagulant is inside syringe 25, protector 10 is removed and an arterial or venous blood sample is taken with the needle which is attached with the needle adapter 26.

In the foregoing description, a specific example has been used to illustrate the invention. However, it is understood by those skilled in the art that certain modifications can be made to this example without departing from the spirit and scope of the invention.

I claim:

1. A needle package comprising: a protector; a needle fitting inside this protector, which needle includes a hub with a passage therethrough communicating with a passage of a cannula; a syringe treating liquid within the protector; and an openable closure sealing off both the passage of the hub and the protector, whereby the closure can be opened and the hub attached to a syringe immediately prior to treating a syringe with the liquid.

2. A needle package as set forth in claim 1, wherein the liquid is an anticoagulant.

3. A needle package as set forth in claim 2, wherein the anticoagulant is heparin.

4. A needle package as set forth in claim 1, wherein the unit is sealed within a vapor barrier enclosure.

5. A needle package as set forth in claim 1, wherein the closure is capable of resealing after puncture for extracting or injecting a material through the closure prior to treating the syringe.

6. A needle package as set forth in claim 1, wherein the closure has an external skirt sealing off a juncture between the protector and needle.

7. A needle package as set forth in claim 6, wherein the skirt also seals off a vent at the juncture between the protector and needle.

8. A needle package as set forth in claim 6, wherein there is a frangible sealing band securing the closure skirt to the protector.

9. A needle package as set forth in claim 1, wherein the closure is removable from the protector and needle for attaching the needle to a syringe.

10. A method of treating a syringe with a protector encased needle with a hub having a passage therethrough communicating with a passage of a cannula, which protector contains a treatment liquid and a closure sealing off both the protector and the passage of the hub, comprising the steps of:
    (a) opening the closure to both the protector and the hub's passage;
    (b) attaching the hub of the needle to a syringe; and
    (c) extracting the treatment liquid into the syringe while the cannula is in the protector.

11. A method as set forth in claim 10, wherein the method further includes:
    (d) removing the protector to leave the needle attached to the syringe.

12. A method as set forth in claim 11, wherein the method further includes:
    (e) collecting a blood sample with the same needle used to treat the syringe.

13. A method as set forth in claim 10, wherein the method also includes sucking a gas into the protector through a vent system as the treatment liquid is extracted into the syringe.

14. A method as set forth in claim 10, wherein the treatment liquid is an anticoagulant.

* * * * *